United States Patent
Trolinder et al.

(10) Patent No.: US 9,382,550 B2
(45) Date of Patent: Jul. 5, 2016

(54) INSECT RESISTANT COTTON PLANTS AND METHODS FOR IDENTIFYING SAME

(75) Inventors: Linda Trolinder, Shallowater, TX (US); Sofie Moens, Zingem (BE); Dimitri Paelinck, Eksaarde (BE); Veerle Habex, Gullegem (BE); Hans Van Herck, Malle (BE)

(73) Assignee: BAYER CROPSCIENCE N.V., Diegem (BE)

( * ) Notice: Subject to any disclaimer, the term of this patent is extended or adjusted under 35 U.S.C. 154(b) by 921 days.

(21) Appl. No.: 13/552,166

(22) Filed: Jul. 18, 2012

(65) Prior Publication Data

US 2013/0059300 A1 Mar. 7, 2013

Related U.S. Application Data

(62) Division of application No. 12/594,363, filed as application No. PCT/EP2008/002667 on Mar. 31, 2008, now Pat. No. 8,247,654.

(60) Provisional application No. 60/923,142, filed on Apr. 12, 2007.

(30) Foreign Application Priority Data

Apr. 5, 2007 (EP) .................... 07075263
Apr. 23, 2007 (EP) .................... 07075299

(51) Int. Cl.
*C12Q 1/68* (2006.01)
*C12P 19/34* (2006.01)
*C07H 21/04* (2006.01)
*C12N 15/82* (2006.01)

(52) U.S. Cl.
CPC .......... *C12N 15/8286* (2013.01); *C12Q 1/6895* (2013.01)

(58) Field of Classification Search
USPC .................... 435/6.1, 6.12, 91.2; 536/23.1
See application file for complete search history.

(56) References Cited

U.S. PATENT DOCUMENTS

| 5,985,557 A | 11/1999 | Prudent et al. |
| 6,001,567 A | 12/1999 | Brow et al. |
| 6,211,431 B1 * | 4/2001 | Boevink et al. ............ 800/278 |

FOREIGN PATENT DOCUMENTS

| WO | WO 98/31822 | 7/1998 |
| WO | WO 03/008440 | 1/2003 |
| WO | WO 03/013224 | 2/2003 |
| WO | WO 03/093484 | 11/2003 |
| WO | WO 2004/048511 | 6/2004 |
| WO | WO 2004/078966 | 9/2004 |
| WO | WO 2006/128568 | 12/2006 |
| WO | WO 2006/128571 | 12/2006 |
| WO | WO 2006/128572 | 12/2006 |
| WO | WO 2006/128573 | 12/2006 |

OTHER PUBLICATIONS

Nucleic acid sequence search reports (Accession No. AR145400, CT617945.*
Choi, Y. et al.; "Adaptor-Aided PCR to Identify T-DNA Junctions in Transgenic Plants;" BioTechniques, vol. 27, pp. 222-226; Aug. 1999.
Edwards, K. et al.; "A Simple and Rapid Method for the Preparation of Plant Genomic DNA for PCR Analysis;" Nucleic Acids Research, vol. 19, No. 6, p. 1349; Jan. 1991.
Liu, Y. et al.; "Efficient Isolation and Mapping of *Arabidopsis thaliana* T-DNA Insert Junctions by Thermal Asymmetric Interlaced PCR;" The Plant Journal, vol. 8, No. 3, pp. 457-463; Feb. 1995.
Parker, C. D. et al.; "Survival Rates of Tobacco Budworm (Lepidoptera: Noctuidae) Larvae Exposed to Transgenic Cottons Expressing Insecticidal Protein of *Bacillus thuringiensis* Berliner;" Journal of Entomological Science, vol. 35, No. 2, pp. 105-117; 1999.
Perlak, F. et al.; "Insect Resistant Cotton Plants"; Biotechnology, vol. 8, pp. 939-943; Oct. 1990.
Unknown; SeedQuest, News Section, pp. 1-3; Feb. 24, 2006.
Unknown; U.S. Environmental Protection Agency Federal Register: Experimental Use Permit; Receipt of Application, vol. 72, No. 10, pp. 1-4; Jan. 17, 2007.
Wilbur, W. J. et al.; "Rapid Similarity Searches of Nucleic Acid and Protein Data Banks;" Proc. Nat'l Acad. Sci., vol. 80, pp. 726-730; Feb. 1983.
Windels, P. et al.; "Development of a Line Specific GMO Detection Method: A Case Study;" Mededelingen Van De Faculteit Landbouwwetenschappen Universiteit Gent 64/5b, vol. 64, No. 5B, pp. 459-462; 1999.
Schunmann Petra H. D. et al. "A Suite of Novel Promoters and Terminators for Plant Biotechnology," Functional Plant Biology, vol. 30, No. 4, Jan. 1, 200, pp. 443-452.

* cited by examiner

*Primary Examiner* — Kenneth R. Horlick
*Assistant Examiner* — Joyce Tung
(74) *Attorney, Agent, or Firm* — Arent Fox LLP

(57) ABSTRACT

The invention provides specific transgenic cotton plants, plant material and seeds, characterized in that these products harbor a specific transformation event at a specific location in the cotton genome. Tools are also provided which allow rapid and unequivocal identification of the event in biological samples.

31 Claims, 3 Drawing Sheets

INSECT RESISTANT COTTON PLANTS AND METHODS FOR IDENTIFYING SAME

CROSS-REFERENCE TO RELATED APPLICATIONS

This application is a divisional application of U.S. application Ser. No. 12/594,363, filed Oct. 2, 2009, which is the U.S. national stage application of PCT/EP2008/02667, filed Mar. 31, 2008, which claims the benefit of EP 07075263.9, filed Apr. 5, 2007, EP 07075299.3, filed Apr. 23, 2007, and U.S. Provisional Application 60/923,142, filed Apr. 12, 2007, the contents of each of which are hereby incorporated by reference in their entireties.

FIELD OF THE INVENTION

This invention relates to transgenic cotton plants, plant material and seeds, characterized by harboring a specific transformation event, particularly by the presence of a gene encoding a protein that confers insect resistance, at a specific location in the cotton genome. The cotton plants of the invention combine the insect resistance phenotype with an agronomic performance, genetic stability and adaptability to different genetic backgrounds equivalent to the non-transformed cotton line in the absence of insects. This invention further provides methods and kits for identifying the presence of plant material comprising specifically transformation event EE-GH5 in biological samples.

BACKGROUND OF THE INVENTION

The phenotypic expression of a transgene in a plant is determined both by the structure of the gene itself and by its location in the plant genome. At the same time the presence of the transgene (in a foreign DNA) at different locations in the genome will influence the overall phenotype of the plant in different ways. The agronomically or industrially successful introduction of a commercially interesting trait in a plant by genetic manipulation can be a lengthy procedure dependent on different factors. The actual transformation and regeneration of genetically transformed plants are only the first in a series of selection steps, which include extensive genetic characterization, breeding, and evaluation in field trials, eventually leading to the selection of an elite event.

Cotton fiber is the single most important textile worldwide. About 80 million acres of cotton are harvested annually across the globe. Cotton is the fifth largest crop in the U.S. in terms of acreage production, with over 15 million acres planted in 2000.

The most damaging insect species feeding on cotton are *Helicoverpa zea* (corn earworm or cotton bollworm), *Helicoverpa armigera* (American bollworm) *Heliothis virescens* (tobacco budworm) and *Helicoverpa punctigera*.

The unequivocal identification of an elite event is becoming increasingly important in view of discussions on Novel Food/Feed, segregation of GMO and non-GMO products and the identification of proprietary material. Ideally, such identification method is both quick and simple, without the need for an extensive laboratory set-up. Furthermore, the method should provide results that allow unequivocal determination of the elite event without expert interpretation, but which hold up under expert scrutiny if necessary. Specific tools for use in the identification of elite event EE-GH5 in biological samples are described herein.

EE-GH5 has been identified as an elite event from a population of transgenic cotton plants in the development of insect resistant cotton (*Gossypium hirsutum*) comprising a gene coding for a insecticidal crystal protein from *Bacillus thuringiensis*. The transgenic cotton plants contain a chimeric gene encoding a Bt insecticidal crystal protein (as described in WO03/093484) under control of a plant-expressible promoter.

Cotton plants comprising a insect resistance gene have been disclosed in the art. However, none of the prior art disclosures teach or suggest the present invention.

SUMMARY OF THE INVENTION

The present invention relates to a transgenic cotton plant, or seed, cells or tissues thereof, comprising, stably integrated into its genome, an expression cassette which comprises a insect resistance gene comprising the coding sequence of the cry1Ab gene (as described in Example 1.1 herein), which is insect resistant and, in the absence of insect pressure, has an agronomic performance which is substantially equivalent to the non-transgenic isogenic line. Under insect pressure, the plant will have a superior agronomic phenotype compared to the non-transgenic plant.

According to the present invention the cotton plant or seed, cells or tissues thereof comprise elite event EE-GH5.

More specifically, the present invention relates to a transgenic cotton plant, seed, cells or tissues thereof, the genomic DNA of which is characterized by the fact that, when analyzed in a PCR identification protocol as described herein, using two primers directed to the 5' or 3' flanking region of EE-GH5 and the foreign DNA, respectively, yields a fragment which is specific for EE-GH5. The primers may be directed against the 5' flanking region within SEQ ID NO: 1 and the foreign DNA respectively such as the primers comprising or consisting of the nucleotide sequence of SEQ ID NO: 7 and SEQ ID NO: 8 respectively, and yield a DNA fragment of between 100 and 700 bp, preferably of about 129 bp. The primers may also be directed against the 3' flanking region within SEQ ID NO: 2 and the foreign DNA respectively such as the primers comprising or consisting of the nucleotide sequence of SEQ ID NO: 3 and SEQ ID NO: 6 respectively, and yield a DNA fragment of between 300 and 700 bp, preferably of about 369 bp.

Reference seed comprising the elite event of the invention has been deposited at the ATCC under accession number PTA-8171. One embodiment of the invention is the seed comprising elite event EE-GH5 deposited as ATTC accession number PTA-8171, which will grow into a cotton plant resistant to insects, particularly *Helicoverpa* sp. or *Heliothis* sp. The seed of ATCC deposit number PTA-8171, is a seed lot consisting of at least about 95% transgenic kernels homozygous for the transgene, comprising the elite event of the invention, which will grow into insect resistant plants, whereby the plants are also glufosinate tolerant plants. The seed can be sown and the growing plants can be treated with glufosinate as described herein to obtain 100% glufosinate tolerant plants, comprising the elite event of the invention. The invention further relates to cells, tissues, progeny, and descendants from a plant comprising the elite event of the invention grown from the seed deposited at the ATCC having accession number PTA-8171. The invention further relates to plants obtainable by propagation of and/or breeding with a cotton plant comprising the elite event of the invention grown from the seed deposited at the ATCC having accession number PTA-8171. The invention also relates to cotton plants comprising elite event EE-GH5.

The invention further relates to a method for identifying a transgenic plant, or cells or tissues thereof, comprising elite event EE-GH5 which method is based on identifying the presence of characterizing DNA sequences or amino acids encoded by such DNA sequences in the transgenic plant, cells or tissues. According to a preferred embodiment of the invention, such characterizing DNA sequences are sequences of 15 bp, preferably 20 bp, most preferably 30 bp or more which comprise the insertion site of the event, i.e. both a part foreign DNA and a part of the cotton genome (either the 5' or 3' flanking region) contiguous therewith, allowing specific identification of the elite event.

The present invention further relates to methods for identifying elite event EE-GH5 in biological samples, which methods are based on primers or probes which specifically recognize the 5' and/or 3' flanking sequence of EE-GH5.

More specifically, the invention relates to a method comprising of amplifying a sequence of a nucleic acid present in biological samples, using a polymerase chain reaction with at least two primers, one of which recognizes the 5' or 3' flanking region of EE-GH5, the other which recognizes a sequence within the foreign DNA, preferably to obtain a DNA fragment of between 100 and 500 bp. The primers may recognize a sequence within the 5' flanking region of EE-GH5 (SEQ ID No. 1, from position 1 to position 98 or SEQ ID No. 16 from position 1 to 563) or within the 3' flanking region of EE-GH5 (complement of SEQ ID No 2 from position 41 to position 452) and a sequence within the foreign DNA (complement of SEQ ID No 1 from position 99 to 334 or SEQ ID No 2 from position 1 to position 40), respectively. The primer recognizing the 5'flanking region may comprise the nucleotide sequence of SEQ ID No. 7 or SEQ ID No. 17 and the primer recognizing a sequence within the foreign DNA may comprise the nucleotide sequence of SEQ ID No. 8, SEQ ID No. 18 or SEQ ID No. 19 described herein. The primer recognizing the 3'flanking region may comprise the nucleotide sequence of SEQ ID No. 6 and the primer recognizing a sequence within the foreign DNA may comprise the nucleotide sequence of SEQ ID No. 3 described herein The present invention more specifically relates to a method for identifying elite event EE-GH5 in biological samples, which method comprises amplifying a sequence of a nucleic acid present in a biological sample, using a polymerase chain reaction with two primers having the nucleotide sequence of SEQ ID No. 3 and SEQ ID No. 6 respectively, to obtain a DNA fragment of about 369 bp.

The current elite event comprises a foreign DNA sequence wherein a slight rearrangement has occurred when compared with the DNA initially used for the transformation procedure, the rearrangement being unique for elite event EE-GH5. Accordingly, the invention also relates to a method for identifying elite event EE-GH5 in biological samples, which method comprises amplifying a sequence of a nucleic acid present in a biological sample, using a polymerase chain reaction with two primers flanking the unique rearrangement of foreign DNA in EE-GH5, such as the primers comprising or having the nucleotide sequence of SEQ ID No 10 and SEQ ID No 11, to obtain a DNA fragment of about 262 bp.

The present invention further relates to the specific flanking sequences of EE-GH5 described herein, which can be used to develop specific identification methods for EE-GH5 in biological samples. Such specific flanking sequences may also be used as reference control material in identification assays. More particularly, the invention relates to the 5' and/or 3' flanking regions of EE-GH5 which can be used for the development of specific primers and probes as further described herein. The invention also relates to nucleic acid molecules spanning the specific rearrangements within the foreign DNA of EE-GH5, such as a nucleic acid molecule comprising the sequence of SEQ ID No. 12 from nucleotide position 52 to nucleotide position 88, or comprising the sequence of SEQ ID No.12. Also suitable as reference material are nucleic acid molecules, preferably of about 369 bp, comprising the sequence which can be amplified by primers having the nucleotide sequence of SEQ ID No. 3 and SEQ ID No. 6

The invention further relates to identification methods for the presence of EE-GH5 in biological samples based on the use of such specific primers or probes. Primers may consist of a nucleotide sequence of 17 to about 200 consecutive nucleotides selected from the nucleotide sequence of SEQ ID No 1 from nucleotide 1 to nucleotide 98 of the nucleotide sequence of SEQ ID No. 16 from nucleotide 1 to nucleotide 563 or the complement of the nucleotide sequence of SEQ ID 2 from nucleotide 41 to nucleotide 452) combined with primers consisting of a nucleotide sequence of 17 to about 200 consecutive nucleotides selected from the complement of the nucleotide sequence of SEQ ID No 1 from nucleotide 99 to nucleotide 334 or the nucleotide sequence of SEQ ID No 2 from nucleotide 1 to nucleotide 40. Primers may also comprise these nucleotide sequences located at their extreme 3' end, and further comprise unrelated sequences or sequences derived from the mentioned nucleotide sequences, but comprising mismatches.

The invention further relates to kits for identifying elite event EE-GH5 in biological samples, said kits comprising at least one primer or probe which specifically recognizes the 5' or 3' flanking region of EE-GH5 or the specific rearrangement within the foreign DNA sequence in EE-GH5.

The kit of the invention may comprise, in addition to a primer which specifically recognizes the 5' or 3' flanking region of EE-GH5, a second primer which specifically recognizes a sequence within the foreign DNA of EE-GH5, for use in a PCR identification protocol. The kits of the invention may comprise at least two specific primers, one of which recognizes a sequence within the 5' flanking region of EE-GH5, and the other which recognizes a sequence within the foreign DNA. The primer recognizing the 5'flanking region may comprises the nucleotide sequence of SEQ ID No. 3 and the primer recognizing the transgene may comprises the nucleotide sequence of SEQ ID No. 6 or any other primer as described herein.

The invention further relates to a kit for identifying elite event EE-GH5 in biological samples, said kit comprising the PCR primers having the nucleotide sequence of SEQ ID No. 3 and SEQ ID No. 6 for use in the EE-GH5 PCR identification protocol described herein. The invention further relates to a kit for identifying elite event EE-GH5 in biological samples, said kit comprising the PCR primers having the nucleotide sequence of SEQ ID No. 10 and SEQ ID No. 11.

The invention also relates to a kit for identifying elite event EE-GH5 in biological samples, which kit comprises a specific probe having a sequence which corresponds (or is complementary to) a sequence having between 80% and 100% sequence identity with a specific region of EE-GH5. Preferably, the sequence of the probe corresponds to a specific region comprising part of the 5' or 3' flanking region of EE-GH5 or to a region corresponding to the rearrangement of foreign DNA specific for EE-GH5. Most preferably the specific probe has (or is complementary to) a sequence having between 80% and 100% sequence identity to the sequence between nucleotide 78 to 119 of SEQ ID No 1 or SEQ ID No. 2 from nucleotide 20 to 61 or SEQ ID 12 from nucleotide 52 to nucleotide 88.

According to another aspect of the invention, DNA sequences are disclosed comprising the insertion site of the event and sufficient length of polynucleotides of both the cotton genomic DNA and the foreign DNA (transgene), so as to be useful as primer or probe for the detection of EE-GH5. Such sequences may comprise at least 9 nucleotides of the cotton genomic DNA and a similar number of nucleotides of the foreign DNA (transgene) of EE-GH5 therewith at each side of the insertion site respectively. Most preferably, such DNA sequences comprise at least 9 nucleotides of the cotton genomic DNA and a similar number of nucleotides of the foreign DNA contiguous with the insertion site in SEQ ID NO: 1 or SEQ ID NO: 2.

The methods and kits encompassed by the present invention can be used for different purposes such as, but not limited to the following: to identify the presence or absence of EE-GH5 in plants, plant material or in products such as, but not limited to food or feed products (fresh or processed) comprising or derived from plant material; additionally or alternatively, the methods and kits of the present invention can be used to identify transgenic plant material for purposes of segregation between transgenic and non-transgenic material; additionally or alternatively, the methods and kits of the present invention can be used to determine the quality (i.e. percentage pure material) of plant material comprising EE-GH5.

The invention further relates to the 5' and/or 3' flanking regions of EE-GH5 as well as to the specific primers and probes developed from the 5' and/or 3' flanking sequences of EE-GH5. The invention also relates to the EE-GH5 specific rearrangement region, as well as to specific primers or probes developed from that region.

The invention also relates to genomic DNA obtained from plants comprising elite event EE-GH5. Such genomic DNA may be used as reference control material in the identification assays herein described.

BRIEF DESCRIPTION OF THE DRAWINGS

The following Examples, not intended to limit the invention to specific embodiments described, may be understood in conjunction with the accompanying Figure, incorporated herein by reference, in which.

DETAILED DESCRIPTION

Figure 1:
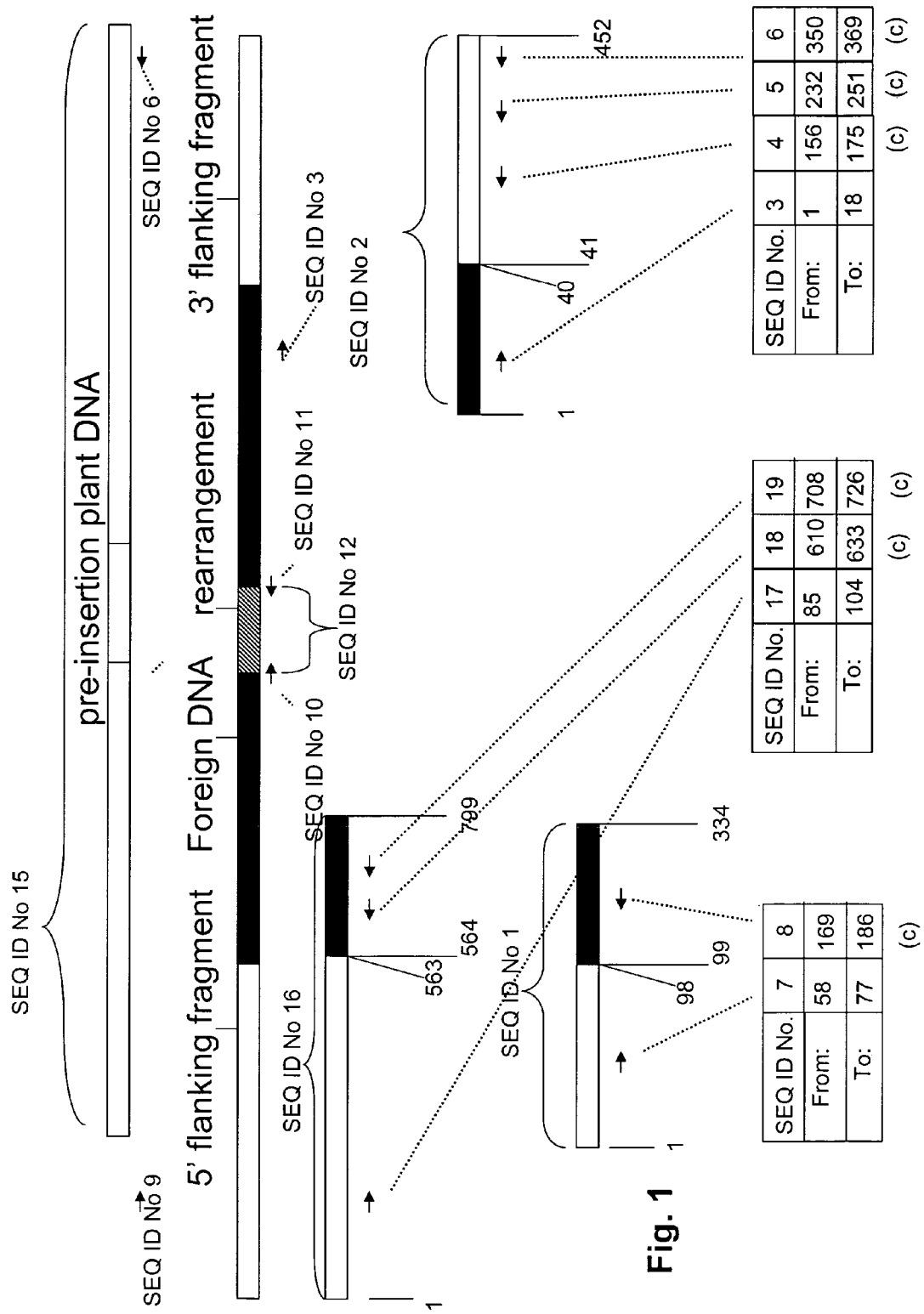
FIG. 1: Represents Schematically the Relationship Between the Cited Nucleotide Sequences and Primers. black bar: foreign DNA; striped black bar: rearrangement in the foreign DNA specific for EE-GH5; light bar: DNA of plant origin; striped light bar: pre-insertion target deletion; arrows: oligonucleotide primers, the figures under the bars represent nucleotide positions; (c) refers to complement of the indicated nucleotide sequence.

The incorporation of a recombinant DNA molecule in the plant genome typically results from transformation of a cell or tissue. The particular site of incorporation is usually due to "random" integration.

The DNA introduced into the plant genome as a result of transformation of a plant cell or tissue with a recombinant DNA or "transforming DNA", and originating from such transforming DNA is hereinafter referred to as "foreign DNA" comprising one or more "transgenes". "Plant DNA" in the context of the present invention will refer to DNA originating from the plant which is transformed. Plant DNA will usually be found in the same genetic locus in the corresponding wild-type plant. The foreign DNA can be characterized by the location and the configuration at the site of incorporation of the recombinant DNA molecule in the plant genome. The site in the plant genome where a recombinant DNA has been inserted is also referred to as the "insertion site" or "target site". Insertion of the recombinant DNA into the region of the plant genome referred to as "pre-insertion plant DNA" can be associated with a deletion of plant DNA, referred to as "target site deletion". A "flanking region" or "flanking sequence" as used herein refers to a sequence of at least 20 bp, preferably at least 50 bp, and up to 5000 bp of DNA different from the introduced DNA, preferably DNA from the plant genome which is located either immediately upstream of and contiguous with or immediately downstream of and contiguous with the foreign DNA. Transformation procedures leading to random integration of the foreign DNA will result in transformants with different flanking regions, which are characteristic and unique for each transformant. When the recombinant DNA is introduced into a plant through traditional crossing, its insertion site in the plant genome, or its flanking regions will generally not be changed. An "insertion region" as used herein refers to the region corresponding to the region of at least 40 bp, preferably at least 100 bp, and up to 10000 bp, encompassed by the sequence which comprises the upstream and/or the downstream flanking region of a foreign DNA in the plant genome. Taking into consideration minor differences due to mutations within a species, an insertion region will retain, upon crossing into a plant of the same species, at least 85%, preferably 90%, more preferably 95%, and most preferably 100% sequence identity with the sequence comprising the upstream and downstream flanking regions of the foreign DNA in the plant originally obtained from transformation.

An event is defined as a (artificial) genetic locus that, as a result of genetic engineering, carries a transgene comprising at least one copy of a gene of interest. The typical allelic states of an event are the presence or absence of the foreign DNA. An event is characterized phenotypically by the expression of the transgene. At the genetic level, an event is part of the genetic make-up of a plant. At the molecular level, an event can be characterized by the restriction map (e.g. as determined by Southern blotting), by the upstream and/or downstream flanking sequences of the transgene, the location of molecular markers and/or the molecular configuration of the transgene. Usually transformation of a plant with a transforming DNA comprising at least one gene of interest leads to a population of transformants comprising a multitude of separate events, each of which is unique.

An elite event, as used herein, is an event which is selected from a group of events, obtained by transformation with the same transforming DNA or by back-crossing with plants obtained by such transformation, based on the expression and stability of the transgene(s) and its compatibility with optimal agronomic characteristics of the plant comprising it. Thus the criteria for elite event selection are one or more, preferably two or more, advantageously all of the following:

a) That the presence of the foreign DNA does not compromise other desired characteristics of the plant, such as those relating to agronomic performance or commercial value;
b) That the event is characterized by a well defined molecular configuration which is stably inherited and for which appropriate tools for identity control can be developed;
c) That the gene(s) of interest show(s) a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use.

It is preferred that the foreign DNA is associated with a position in the plant genome that allows easy introgression into desired commercial genetic backgrounds.

The status of an event as an elite event is confirmed by introgression of the elite event in different relevant genetic backgrounds and observing compliance with one, two or all of the criteria e.g. a), b) and c) above.

An "elite event" thus refers to a genetic locus comprising a foreign DNA, which answers to the above-described criteria. A plant, plant material or progeny such as seeds can comprise one or more elite events in its genome.

The tools developed to identify an elite event or the plant, plant material comprising an elite event, or products which comprise plant material comprising the elite event are based on the specific genomic characteristics of the elite event, such as, a specific restriction map of the genomic region comprising the foreign DNA, molecular markers or the sequence of the flanking region(s) of the foreign DNA.

Once one or both of the flanking regions of the foreign DNA have been sequenced, primers and probes can be developed which specifically recognize this (these) sequence(s) in the nucleic acid (DNA or RNA) of a sample by way of a molecular biological technique. For instance a PCR method can be developed to identify the elite event in biological samples (such as samples of plants, plant material or products comprising plant material). Such a PCR is based on at least two specific "primers" one recognizing a sequence within the 5' or 3' flanking region of the elite event and the other recognizing a sequence within the foreign DNA. The primers preferably have a sequence of between 15 and 35 nucleotides which under optimized PCR conditions "specifically recognize" a sequence within the 5' or 3' flanking region of the elite event and the foreign DNA of the elite event respectively, so that a specific fragment ("integration fragment" or discriminating amplicon) is amplified from a nucleic acid sample comprising the elite event. This means that only the targeted integration fragment, and no other sequence in the plant genome or foreign DNA, is amplified under optimized PCR conditions.

PCR primers suitable for the invention may be the following:

oligonucleotides ranging in length from 17 nt to about 100 nt, comprising a nucleotide sequence of at least 17 consecutive nucleotides, preferably 20 consecutive nucleotides selected from the 5' flanking sequence (SEQ ID No 1 from nucleotide 1 to nucleotide 98 or SEQ ID No 16 from nucleotide 1 to 563) at their 3' end (primers recognizing 5' flanking sequences); or oligonucleotides ranging in length from 17 nt to about 200 nt, comprising a nucleotide sequence of at least 17 consecutive nucleotides, preferably 20 consecutive nucleotides, selected from the 3' flanking sequence (complement of SEQ ID No 2 from nucleotide 41 to nucleotide 452) at their 3' end (primers recognizing 3' flanking sequences); or oligonucleotides ranging in length from 17 nt to about 200 nt, comprising a nucleotide sequence of at least 17 consecutive nucleotides, preferably 20 nucleotides selected from the inserted DNA sequences (complement of SEQ ID No 1 from nucleotide 99 to nucleotide 334) at their 3' end (primers recognizing foreign DNA) or oligonucleotides ranging in length from 17 nt to about 40 nt, comprising a nucleotide sequence of at least 17 consecutive nucleotides, preferably 20 nucleotides selected from the inserted DNA sequences (SEQ ID No 2 from nucleotide 1 to nucleotide 40)

The primers may of course be longer than the mentioned 17 consecutive nucleotides, and may e.g. be 20, 21, 30, 35, 50, 75, 100, 150, 200 nt long or even longer. The primers may entirely consist of nucleotide sequence selected from the mentioned nucleotide sequences of flanking sequences and foreign DNA sequences. However, the nucleotide sequence of the primers at their 5' end (i.e. outside of the 3'-located 17 consecutive nucleotides) is less critical. Thus, the 5' sequence of the primers may consist of a nucleotide sequence selected from the flanking sequences or foreign DNA, as appropriate, but may contain several (e.g. 1, 2, 5, 10 mismatches). The 5' sequence of the primers may even entirely consist of a nucleotide sequence unrelated to the flanking sequences or foreign DNA, such as e.g. a nucleotide sequence representing restriction enzyme recognition sites. Such unrelated sequences or flanking DNA sequences with mismatches should preferably be not longer than 100, more preferably not longer than 50 or even 25 nucleotides.

Moreover, suitable primers may comprise or consist of a nucleotide sequence at their 3' end spanning the joining region between the plant DNA derived sequences and the foreign DNA sequences (located at nucleotides 98-99 in SEQ ID No 1 and nucleotides 40-41 in SEQ ID No 2) provided the mentioned 3'-located 17 consecutive nucleotides are not derived exclusively from either the foreign DNA or plant-derived sequences in SEQ ID No 1 or 2.

It will also be immediately clear to the skilled artisan that properly selected PCR primer pairs should also not comprise sequences complementary to each other.

For the purpose of the invention, the "complement of a nucleotide sequence represented in SEQ ID No: X" is the nucleotide sequence which can be derived from the represented nucleotide sequence by replacing the nucleotides through their complementary nucleotide according to Chargaff's rules (A⇔T; G⇔C) and reading the sequence in the 5' to 3' direction, i.e in opposite direction of the represented nucleotide sequence.

Examples of suitable primers are the oligonucleotide sequences of SEQ ID No 7 or SEQ ID No 17 (5' flanking sequence recognizing primers), SEQ ID No 8, SEQ ID No 18 or SEQ ID No 19 (foreign DNA recognizing primers for use with the 5' flanking sequence recognizing primers), SEQ ID No 3 (foreign DNA recognizing primers for use with the 3' flanking sequence recognizing primers), SEQ ID No 4, SEQ ID No 5, SEQ ID No 6 (3' flanking sequence recognizing primers) and SEQ ID Nos 10 and 11 (primers recognizing the specific foreign DNA rearrangement in EE-GH5).

Other examples of suitable oligonucleotide primers comprise at their 3' end the following sequences or consist of such sequences:

a. 5' flanking sequence recognizing primers:
- the nucleotide sequence of SEQ ID No 1 from nucleotide 58 to nucleotide 77
- the nucleotide sequence of SEQ ID No 16 from nucleotide 85 to nucleotide 104
- the nucleotide sequence of SEQ ID No 16 from nucleotide 150 to nucleotide 166
- the nucleotide sequence of SEQ ID No 16 from nucleotide 150 to nucleotide 171
- the nucleotide sequence of SEQ ID No 16 from nucleotide 154 to nucleotide 171
- the nucleotide sequence of SEQ ID No 16 from nucleotide 87 to nucleotide 104
- the nucleotide sequence of SEQ ID No 16 from nucleotide 189 to nucleotide 206 b. foreign DNA sequence recognizing primers for use with 5' flanking sequence recognizing primers:
- the complement of the nucleotide sequence of SEQ ID No 1 from nucleotide 149 to nucleotide 170
- the complement of the nucleotide sequence of SEQ ID No 1 from nucleotide 169 to nucleotide 186
- the complement of the nucleotide sequence of SEQ ID No 1 from nucleotide 193 to nucleotide 212
- the complement of the nucleotide sequence of SEQ ID No 1 from nucleotide 161 to nucleotide 178
- the complement of the nucleotide sequence of SEQ ID No 1 from nucleotide 194 to nucleotide 211
- the complement of the nucleotide sequence of SEQ ID No 1 from nucleotide 193 to nucleotide 211
- the complement of the nucleotide sequence of SEQ ID No 1 from nucleotide 163 to nucleotide 185
- the complement of the nucleotide sequence of SEQ ID No 1 from nucleotide 194 to nucleotide 210
- the complement of the nucleotide sequence of SEQ ID No 1 from nucleotide 193 to nucleotide 210
- the complement of the nucleotide sequence of SEQ ID No 1 from nucleotide 193 to nucleotide 209 c. 3' flanking sequence recognizing primers:
- the complement of the nucleotide sequence of SEQ ID No 2 from nucleotide 149 to nucleotide 168
- the complement of the nucleotide sequence of SEQ ID No 2 from nucleotide 154 to nucleotide 173
- the complement of the nucleotide sequence of SEQ ID No 2 from nucleotide 140 to nucleotide 159
- the complement of the nucleotide sequence of SEQ ID No 2 from nucleotide 141 to nucleotide 160
- the complement of the nucleotide sequence of SEQ ID No 2 from nucleotide 147 to nucleotide 166
- the complement of the nucleotide sequence of SEQ ID No 2 from nucleotide 148 to nucleotide 167
- the complement of the nucleotide sequence of SEQ ID No 2 from nucleotide 149 to nucleotide 167
- the complement of the nucleotide sequence of SEQ ID No 2 from nucleotide 153 to nucleotide 172
- the complement of the nucleotide sequence of SEQ ID No 2 from nucleotide 154 to nucleotide 174
- the complement of the nucleotide sequence of SEQ ID No 2 from nucleotide 160 to nucleotide 177
- the complement of the nucleotide sequence of SEQ ID No 2 from nucleotide 232 to nucleotide 251
- the complement of the nucleotide sequence of SEQ ID No 2 from nucleotide 140 to nucleotide 160
- the complement of the nucleotide sequence of SEQ ID No 2 from nucleotide 141 to nucleotide 161
- the complement of the nucleotide sequence of SEQ ID No 2 from nucleotide 147 to nucleotide 165
- the complement of the nucleotide sequence of SEQ ID No 2 from nucleotide 149 to nucleotide 166
- the complement of the nucleotide sequence of SEQ ID No 2 from nucleotide 148 to nucleotide 166
- the complement of the nucleotide sequence of SEQ ID No 2 from nucleotide 147 to nucleotide 167
- the complement of the nucleotide sequence of SEQ ID No 2 from nucleotide 148 to nucleotide 168
- the complement of the nucleotide sequence of SEQ ID No 2 from nucleotide 153 to nucleotide 173
- the complement of the nucleotide sequence of SEQ ID No 2 from nucleotide 154 to nucleotide 175
- the complement of the nucleotide sequence of SEQ ID No 2 from nucleotide 156 to nucleotide 175
- the complement of the nucleotide sequence of SEQ ID No 2 from nucleotide 232 to nucleotide 250
- the complement of the nucleotide sequence of SEQ ID No 2 from nucleotide 140 to nucleotide 157
- the complement of the nucleotide sequence of SEQ ID No 2 from nucleotide 140 to nucleotide 161
- the complement of the nucleotide sequence of SEQ ID No 2 from nucleotide 141 to nucleotide 162
- the complement of the nucleotide sequence of SEQ ID No 2 from nucleotide 148 to nucleotide 165
- the complement of the nucleotide sequence of SEQ ID No 2 from nucleotide 149 to nucleotide 165
- the complement of the nucleotide sequence of SEQ ID No 2 from nucleotide 147 to nucleotide 168
- the complement of the nucleotide sequence of SEQ ID No 2 from nucleotide 148 to nucleotide 169
- the complement of the nucleotide sequence of SEQ ID No 2 from nucleotide 156 to nucleotide 174
- the complement of the nucleotide sequence of SEQ ID No 2 from nucleotide 153 to nucleotide 174
- the complement of the nucleotide sequence of SEQ ID No 2 from nucleotide 232 to nucleotide 249
- the complement of the nucleotide sequence of SEQ ID No 2 from nucleotide 234 to nucleotide 251
- the complement of the nucleotide sequence of SEQ ID No 2 from nucleotide 141 to nucleotide 163
- the complement of the nucleotide sequence of SEQ ID No 2 from nucleotide 148 to nucleotide 164
- the complement of the nucleotide sequence of SEQ ID No 2 from nucleotide 147 to nucleotide 169
- the complement of the nucleotide sequence of SEQ ID No 2 from nucleotide 153 to nucleotide 175
- the complement of the nucleotide sequence of SEQ ID No 2 from nucleotide 156 to nucleotide 177
- the complement of the nucleotide sequence of SEQ ID No 2 from nucleotide 181 to nucleotide 198
- the complement of the nucleotide sequence of SEQ ID No 2 from nucleotide 181 to nucleotide 202
- the complement of the nucleotide sequence of SEQ ID No 2 from nucleotide 234 to nucleotide 250
- the complement of the nucleotide sequence of SEQ ID No 2 from nucleotide 140 to nucleotide 162
- the complement of the nucleotide sequence of SEQ ID No 2 from nucleotide 181 to nucleotide 203 d. foreign DNA sequence recognizing primers for use with 3' flanking sequence recognizing primers:
- the nucleotide sequence of SEQ ID No 2 from nucleotide 30 to nucleotide 49
- the nucleotide sequence of SEQ ID No 2 from nucleotide 30 to nucleotide 48 the nucleotide sequence of SEQ ID No 2 from nucleotide 32 to nucleotide 48 the nucleotide sequence of SEQ ID No 2 from nucleotide 32 to nucleotide 49 the nucleotide sequence of SEQ ID No 2 from nucleotide 31 to nucleotide 49 the nucleotide sequence of SEQ ID No 2 from nucleotide 31 to nucleotide 48 the nucleotide sequence of SEQ ID No 2 from nucleotide 30 to nucleotide 46

As used herein, "the nucleotide sequence of SEQ ID No. Z from position X to position Y" indicates the nucleotide sequence including both nucleotide endpoints.

Preferably, the amplified fragment has a length of between 50 and 500 nucleotides, most preferably of between 100 and 350 nucleotides. The specific primers may have a sequence which is between 80 and 100% identical to a sequence within the 5' or 3' flanking region of the elite event and the foreign DNA of the elite event, respectively, provided the mismatches still allow specific identification of the elite event with these primers under optimized PCR conditions. The range of allowable mismatches however, can easily be determined experimentally and are known to a person skilled in the art.

The following table exemplifies the sizes of expected DNA amplicons (or integration fragments) with selected pairs of PCR primers.

| Primer 1 | From position | Primer 2 | To position | Length amplicon |
|---|---|---|---|---|
| HVH024 | 58 | DPA312 | 186 | 128 |
| GHI057 | 1 | MAE115 | 175 | 175 |
| GHI057 | 1 | HVH022 | 251 | 251 |
| GHI057 | 1 | GHI065 | 369 | 369 |

Detection of integration fragments can occur in various ways e.g. via size estimation after gel analysis. The integration fragments may also be directly sequenced. Other sequence specific methods for detection of amplified DNA fragments are also known in the art.

As the sequence of the primers and their relative location in the genome are unique for the elite event, amplification of the integration fragment will occur only in biological samples comprising (the nucleic acid of) the elite event. Preferably when performing a PCR to identify the presence of EE-GH5 in unknown samples, a control is included of a set of primers with which a fragment within a "housekeeping gene" of the plant species of the event can be amplified. Housekeeping genes are genes that are expressed in most cell types and which are concerned with basic metabolic activities common to all cells. Preferably, the fragment amplified from the housekeeping gene is a fragment which is larger than the amplified integration fragment. Depending on the samples to be analyzed, other controls can be included.

Standard PCR protocols are described in the art, such as in 'PCR Applications Manual" (Roche Molecular Biochemicals, 2nd Edition, 1999) and other references. The optimal conditions for the PCR, including the sequence of the specific primers, is specified in a "PCR identification protocol" for each elite event. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase and annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Alternatively, specific primers can be used to amplify an integration fragment that can be used as a "specific probe" for identifying EE-GH5 in biological samples. Contacting nucleic acid of a biological sample, with the probe, under conditions which allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of EE-GH5. Such identification methods based on hybridization with a specific probe (either on a solid phase carrier or in solution) have been described in the art. The specific probe is preferably a sequence which, under optimized conditions, hybridizes specifically to a region within the 5' or 3' flanking region of the elite event and preferably also comprising part of the foreign DNA contiguous therewith (hereinafter referred to as "specific region"). Preferably, the specific probe comprises a sequence of between 50 and 500 bp, preferably of 100 to 350 bp which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 15 to about 100 contiguous nucleotides identical (or complementary) to a specific region of the elite event.

Oligonucleotides suitable as PCR primers for detection of the elite event EE-GH5 can also be used to develop a PCR-based protocol to determine the zygosity status of the elite event. To this end, two primers recognizing the wild-type locus are designed in such a way that they are directed towards each other and have the insertion site located in between the primers. These primers may be primers specifically recognizing the 5' and 3' flanking sequences contained within SEQ ID NO 1 or 2, respectively. These primers may also be primers specifically recognizing the 5' or 3' flanking sequence (such as a primer having the nucleotide sequence of SEQ ID No 7 or SEQ ID Nos 4-6) as well as a primer recognizing the region deleted during EE-GH5 insertion within the pre-insertion plant DNA). This set of primers, together with a third primer complementary to transforming DNA sequences (such as a primer having the nucleotide sequence of SEQ ID No 3) allow diagnostic PCR amplification of the EE-GH5 specific locus, as well as of the wt locus. If the plant is homozygous for the transgenic locus or the corresponding wt locus, the diagnostic PCR will give rise to a single PCR product typical, preferably typical in length, for either the transgenic or wt locus. If the plant is hemizygous for the transgenic locus, two locus specific PCR products will appear, reflecting both the amplification of the transgenic and wt locus.

Furthermore, detection methods specific for elite event EE-GH5 which differ from PCR based amplification methods can also be developed using the elite event specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage, incorporated herein by reference). To this end, the target sequence may hybridized with a labeled first nucleic acid oligonucleotide comprising the nucleotide sequence of SEQ ID No 1 from nucleotide 99 to nucleotide 116 or its complement or said labeled nucleic acid probe comprising the nucleotide sequence of SEQ ID No 2 from nucleotide 23 to nucleotide 40 or its complement and is further hybridized with a second nucleic acid oligonucleotide comprising the nucleotide sequence of SEQ ID No 1 from nucleotide 81 to nucleotide 98 or its complement or said labeled nucleic acid probe comprising the nucleotide sequence of SEQ ID No 2 from nucleotide 41 to nucleotide 58 or its complement, wherein the first and second oligonucleotide overlap by at least one nucleotide. The duplex or triplex structure which is produced by this hybridization allows selective probe cleavage with an enzyme (Cleavase®) leaving the target sequence intact. The cleaved labeled probe is subsequently detected, potentially via an intermediate step resulting in further signal amplification.

A "kit" as used herein refers to a set of reagents for the purpose of performing the method of the invention, more particularly, the identification of the elite event EE-GH5 in biological samples or the determination of the zygosity status of EE-GH5 containing plant material. More particularly, a preferred embodiment of the kit of the invention comprises at least one or two specific primers, as described above for identification of the elite event, or three specific primers for the determination of the zygosity status. Optionally, the kit can further comprise any other reagent described herein in the PCR identification protocol. Alternatively, according to another embodiment of this invention, the kit can comprise a specific probe, as described above, which specifically hybridizes with nucleic acid of biological samples to identify the presence of EE-GH5 therein. Optionally, the kit can further comprise any other reagent (such as but not limited to hybridizing buffer, label) for identification of EE-GH5 in biological samples, using the specific probe.

The kit of the invention can be used, and its components can be specifically adjusted, for purposes of quality control (e.g., purity of seed lots), detection of the presence or absence of the elite event in plant material or material comprising or derived from plant material, such as but not limited to food or feed products.

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983, Proc. Nat. Acad. Sci. USA 80:726) using a window-size of 20 nucleotides, a word length of 4 nucleotides, and a gap penalty of 4. Computer-assisted analysis and interpretation of sequence data, including sequence alignment as described above, can, e.g., be conveniently performed using the sequence analysis software package of the Genetics Computer Group (GCG, University of Wisconsin Biotechnology center). Sequences are indicated as "essentially similar" when such sequences have a sequence identity of at least about 75%, particularly at least about 80%, more particularly at least about 85%, quite particularly about 90%, especially about 95%, more especially about 100%. It is clear than when RNA sequences are said to be essentially similar or have a certain degree of sequence identity with DNA sequences, thymidine (T) in the DNA sequence is considered equal to uracil. (U) in the RNA sequence.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in the elite event under the conditions set forth in the method (such as the conditions of the PCR identification protocol), whereby the specificity is determined by the presence of positive and negative controls.

The term "hybridizing" as used herein when referring to specific probes, refer to the fact that the probe binds to a specific region in the nucleic acid sequence of the elite event under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbour Laboratory Press, NY) which for instance can comprise the following steps: 1) immobilizing plant genomic DNA fragments on a filter, 2) prehybridizing the filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS, 3) adding the hybridization probe which has been labeled, 4) incubating for 16 to 24 hours, 5) washing the filter for 20 min. at room temperature in 1×SSC, 0.1% SDS, 6) washing the filter three times for 20 min. each at 68° C. in 0.2×SSC, 0.1% SDS, and 7) exposing the filter for 24 to 48 hours to X-ray film at −70° C. with an intensifying screen.

As used in herein, a biological samples is a sample of a plant, plant material or products comprising plant material. The term "plant" is intended to encompass cotton (*Gossypium hirsitum*) plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. It is understood that, in the context of the present invention, such biological samples are tested for the presence of nucleic acids specific for EE-GH5, implying the presence of nucleic acids in the samples. Thus the methods referred to herein for identifying elite event EE-GH5 in biological samples, relate to the identification in biological samples of nucleic acids which comprise the elite event.

As used herein "comprising" is to be interpreted as specifying the presence of the stated features, integers, steps, reagents or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence which is functionally or structurally defined, may comprise additional DNA sequences, etc.

The present invention also relates to the development of an elite event EE-GH5 in cotton to the plants comprising this event, the progeny obtained from these plants and to the plant cells, or plant material derived from this event. Plants comprising elite event EE-GH5 were obtained described in example 1.

Cotton plants or plant material comprising EE-GH5 can be identified according to the PCR identification protocol described for EE-GH5 in Example 2. Briefly, cotton genomic DNA present in the biological sample is amplified by PCR using a primer which specifically recognizes a sequence within the 5' or 3' flanking sequence of EE-GH5 such as the primer with the sequence of SEQ ID NO: 6, and a primer which recognizes a sequence in the foreign DNA, such as the primer with the sequence of SEQ ID NO: 3. DNA primers which amplify part of an endogenous cotton sequence are used as positive control for the PCR amplification. If upon PCR amplification, the material yields a fragment of the expected size, the material contains plant material from a cotton plant harboring elite event EE-GH5.

Plants harboring EE-GH5 are characterized by their insect resistance, as well as by their glufosinate tolerance. Plants harboring EE-GH5 are also characterized by having agronomical characteristics that are comparable to commercially available varieties of cotton in the US, in the absence of insect pressure. It has been observed that the presence of a foreign DNA in the insertion region of the cotton plant genome described herein, confers particularly interesting phenotypic and molecular characteristics to the plants comprising this event.

The following examples describe the identification of elite event EE-GH5 and the development of tools for the specific identification of elite event EE-GH5 in biological samples.

Unless states otherwise in the Examples, all recombinant techniques are carried out according to standard protocols as described in "Sambrook J and Russell D W (eds.) (2001) Molecular Cloning: A Laboratory Manual, 3rd Edition, Cold Spring Harbor Laboratory Press, New York" and in "Ausubel F A, Brent R, Kingston R E, Moore D D, Seidman J G, Smith J A and Struhl K (eds.) (2006) Current Protocols in Molecular Biology. John Wiley & Sons, New York".

Standard materials and references are described in "Croy R D D (ed.) (1993) Plant Molecular Biology LabFax, BIOS Scientific Publishers Ltd., Oxford and Blackwell Scientific Publications, Oxford" and in "Brown T A, (1998) Molecular Biology LabFax, 2nd Edition, Academic Press, San Diego". Standard materials and methods for polymerase chain reactions (PCR) can be found in "McPherson M J and Møller S G (2000) PCR (The Basics), BIOS Scientific Publishers Ltd., Oxford" and in "PCR Applications Manual, 3rd Edition (2006), Roche Diagnostics GmbH, Mannheim or www.roche-applied-science.com"

In the description and examples, reference is made to the following sequences:
SEQ ID No. 1: nucleotide sequence comprising a 5' flanking region of EE-GH5
SEQ ID No. 2: nucleotide sequence comprising a 3' flanking region of EE-GH5
SEQ ID No. 3: primer GHI057
SEQ ID No. 4: primer MAE115
SEQ ID No. 5: primer HVH022
SEQ ID No. 6: primer GHI065
SEQ ID No. 7: primer HVH024
SEQ ID No. 8: primer DPA312
SEQ ID No. 9: primer GHI066
SEQ ID No. 10: primer GHI047
SEQ ID No. 11: primer GHI048
SEQ ID No. 12: Nucleotide sequence of the fragment amplified from cotton DNA comprising EE-GH5 using GHI047 and GHI048
SEQ ID No. 13: primer 1 for amplification of control fragment
SEQ ID No. 14: primer 2 for amplification of control fragment
SEQ ID No. 15: Nucleotide sequence of the plant genomic target sequence prior to insertion of EE-GH5
SEQ ID No. 16: Nucleotide sequence comprising a 5' flanking region of EE-GH5 (long)
SEQ ID No. 17: primer HVH036
SEQ ID No. 18: primer SHA028
SEQ ID No. 19: primer MAE067

EXAMPLES

1. Identification of Elite Event EE-GH5

Insect-resistant cotton was developed by transformation of cotton with a vector comprising the coding sequence of a modified cry1ab gene under the control of a Subterranean Clover stunt virus S7 promoter.

Elite event EE-GH5 was selected based on an extensive selection procedure based on good expression and stability of the insect resistance gene and its compatibility with optimal agronomic characteristics such as plant height, height to node, boll retention, stand, vigor, fiber length, fiber strength and lint yield were evaluated.

The selected event was introduced into different commercial genetic backgrounds, and results of field trials on different locations were compared. Plants were challenged with insect pests using different treatments. Plants exhibited good insect control.

Furthermore, the event had normal leaf, flower and boll morphology, excellent fertility, and showed no disease or abnormal insect susceptibility in multiple genetic backgrounds. During introgression into multiple genetic backgrounds no aberrant problems or abnormalities were observed.

2. Identification of the Flanking Regions of Elite Event EE-GH5

The sequence of the regions flanking the foreign DNA in the EE-GH5 elite event was determined using the thermal asymmetric interlaced (TAIL-) PCR method described by Liu et al. (1995, Plant J. 8(3):457-463) where possible. This method utilizes three nested primers in successive reactions together with a shorter arbitrary degenerate primer so that the relative amplification efficiencies of specific and non-specific products can be thermally controlled. The specific primers were selected for annealing to the border of the foreign DNA and based on their annealing conditions. A small amount (5 µl) of unpurified, secondary and tertiary, PCR products were analyzed on a 1% agarose gel. The tertiary PCR product was purified and sequenced.

2.1. Right (5') Flanking Region

The fragment identified as comprising the 5' flanking region was sequenced (SEQ ID No. 1). The sequence between nucleotide 1 and 98 corresponds to plant DNA, while the sequence between nucleotide 99 and 334 corresponds to foreign DNA. A longer fragment comprising the 5' flanking region was also sequenced (SEQ ID No. 16). The sequence between nucleotide 1 and 563 corresponds to plant DNA, while the sequence between nucleotide 564 and 799 corresponds to foreign DNA 2.2. Left (3') Flanking Region The fragment identified as comprising the 3' flanking region obtained by the TAIL-PCR method was sequenced (SEQ ID No. 2). The sequence between nucleotide 1 and 40 corresponds to foreign DNA, while the sequence between nucleotide 41 and 452 corresponds to plant DNA.

2.3. Region Comprising EE-GH5 Specific Rearrangement in Foreign DNA.

The nucleotide sequence of a region comprising the EE-GH5 specific rearrangement in the foreign DNA was identified (SEQ ID No. 12). The region between nucleotide positions 52 and 88 were identified as being rearranged when compared with the foreign DNA used to obtain transformants from which elite event EE-GH5 was selected.

3. Development of Polymerase Chain Reaction Identification Protocols for EE-GH5

3.1. Primers

Specific primers were developed which recognize sequences within the elite event.

More particularly, two primers were developed which recognize sequences flanking the EE-GH5 specific rearrangement in the foreign DNA. The primers span a sequence of about 262 bp. The following primers were found to give particularly clear and reproducible results in a PCR reaction on EE-GH5 DNA:

```
                                        (SEQ ID No.: 10)
GHI047:  5'-TgC.CTC.TTg.AAC.TgT.AgC-3'

(SEQ ID No.: 11)
GHI048:  5'-ACT.TgC.AgT.TgC.TgA.TgA.Tg-3'
```

Alternatively, a primer was developed which recognizes a sequence within the 5' flanking region of EE-GH5. A second primer was then selected within the sequence of the foreign DNA so that the primers span a sequence of about 369 nucleotides. The following primers were found to give particularly clear and reproducible results in a PCR reaction on EE-GH5 DNA:

```
                                        (SEQ ID No.: 6)
GHI065:    5'-ggg.CCg.gAT.AAA.ATT.AgC.CT-3'

(target: plant DNA)

(SEQ ID No.: 3)
GHI057:    5'-ATA.gCg.CgC.AAA.CTA.ggA-3'

(target: insert DNA)
```

Primers targeting an endogenous sequence are preferably included in the PCR cocktail. These primers serve as an internal control in unknown samples and in the DNA positive control. A positive result with the endogenous primer-pair demonstrates that there is ample DNA of adequate quality in the genomic DNA preparation for a PCR product to be generated. The endogenous primers were selected to recognize a housekeeping gene in cotton:

```
                                        (SEQ ID No.: 13)
GHI001:  5'-AAC.CTA.ggC.TgC.TgA.Agg.AgC-3'

(SEQ ID No.: 14)
GHI002:  5'-CAA.CTC.CTC.CAg.TCA.TCT.CCg-3'
```

3.2. Amplified Fragments

The expected amplified fragments in the PCR reaction are:
For primer pair GHI001-GHI002: 445 bp (endogenous control)
For primer pair GH1047-GHI048: 262 bp (EE-GH5 elite Event)
For primer pair GHI057-GH1065: 369 bp (EE-GH5 elite Event)

3.3. Template DNA

Template DNA was prepared from a leaf punch according to Edwards et al. (Nucleic Acid Research, 19, p 1349, 1991). When using DNA prepared with other methods, a test run utilizing different amounts of template should be done. Usually 50 ng of genomic template DNA yields the best results.

3.4. Assigned Positive and Negative Controls

To avoid false positives or negatives, it was determined that the following positive and negative controls should be included in a PCR run:

Master Mix control (DNA negative control). This is a PCR in which no DNA is added to the reaction. When the expected result, no PCR products, is observed this indicates that the PCR cocktail was not contaminated with target DNA.

A DNA positive control (genomic DNA sample known to contain the transgenic sequences). Successful amplification of this positive control demonstrates that the PCR was run under conditions which allow for the amplification of target sequences.

A wild-type DNA control. This is a PCR in which the template DNA provided is genomic DNA prepared from a non-transgenic plant. When the expected result, no amplification of a transgene PCR product but amplification of the endogenous PCR product, is observed this indicates that there is no detectable transgene background amplification in a genomic DNA sample.

3.5. PCR Conditions

Optimal results were obtained under the following conditions:

the PCR mix for 25 µl reactions contains:
2.5 µl template DNA
2.5 µl 10× Amplification Buffer (supplied by the manufacturer with the Taq polymerase)
0.5 µl 10 mM dNTP's
0.4 µl GHI001 (10 pmoles/µl)
0.4 µl GHI002 (10 pmoles/µl)
0.7 µl GHI047 (10 pmoles/µl) or GHI057 (PCR protocol 2)
0.7 µl GHI048 (10 pmoles/µl) or GHI065 (PCR protocol 2)
0.1 µl Taq DNA polymerase (5 units/µl)
water up to 25 µl the thermocycling profile to be followed for optimal results is the following:
4 min. at 95° C.
Followed by:
1 min. at 95° C.
1 min. at 57° C.
2 min. at 72° C.
For 5 cycles
Followed by:
30 sec. at 92° C.
30 sec. at 57° C.
1 min. at 72° C.
For 25 cycles
Followed by:
10 minutes at 72° C.

3.6. Agarose Gel Analysis

To optimally visualise the results of the PCR it was determined that between 10 and 20 µl of the PCR samples should be applied on a 1.5% agarose gel (Tris-borate buffer) with an appropriate molecular weight marker (e.g. 100 bp ladder PHARMACIA).

3.7. Validation of the Results

It was determined that data from transgenic plant DNA samples within a single PCR run and a single PCR cocktail should not be acceptable unless 1) the DNA positive control shows the expected PCR products (transgenic and endogenous fragments), 2) the DNA negative control is negative for PCR amplification (no fragments) and 3) the wild-type DNA control shows the expected result (endogenous fragment amplification).

When following the PCR Identification Protocol for EE-GH5 as described above, lanes showing visible amounts of the transgenic and endogenous PCR products of the expected sizes, indicate that the corresponding plant from which the genomic template DNA was prepared, has inherited the EE-GH5 elite event. Lanes not showing visible amounts of either of the transgenic PCR products and showing visible amounts of the endogenous PCR product, indicate that the corresponding plant from which the genomic template DNA was prepared, does not comprise the elite event. Lanes not showing visible amounts of the endogenous and transgenic PCR products, indicate that the quality and/or quantity of the genomic DNA didn't allow for a PCR product to be generated. These plants cannot be scored. The genomic DNA preparation should be repeated and a new PCR run, with the appropriate controls, has to be performed.

3.8. Use of Discriminating PCR Protocol to Identify EE-GH5

Before attempting to screen unknowns, a test run, with all appropriate controls, has to be performed. The developed protocol might require optimization for components that may differ between labs (template DNA preparation, Taq DNA polymerase, quality of the primers, dNTP's, thermocyler, etc.).

Amplification of the endogenous sequence plays a key role in the protocol. One has to attain PCR and thermocycling conditions that amplify equimolar quantities of both the endogenous and transgenic sequence in a known transgenic genomic DNA template. Whenever the targeted endogenous fragment is not amplified or whenever the targeted sequences are not amplified with the same ethidium bromide staining intensities, as judged by agarose gel electrophoresis, optimization of the PCR conditions may be required.

Leaf material from a number of cotton plants, some of which comprising EE-GH5 were tested according to the above-described protocol. Samples from elite event EE-GH5 and from cotton wild-type were taken as positive and negative controls, respectively.

Figure 2:
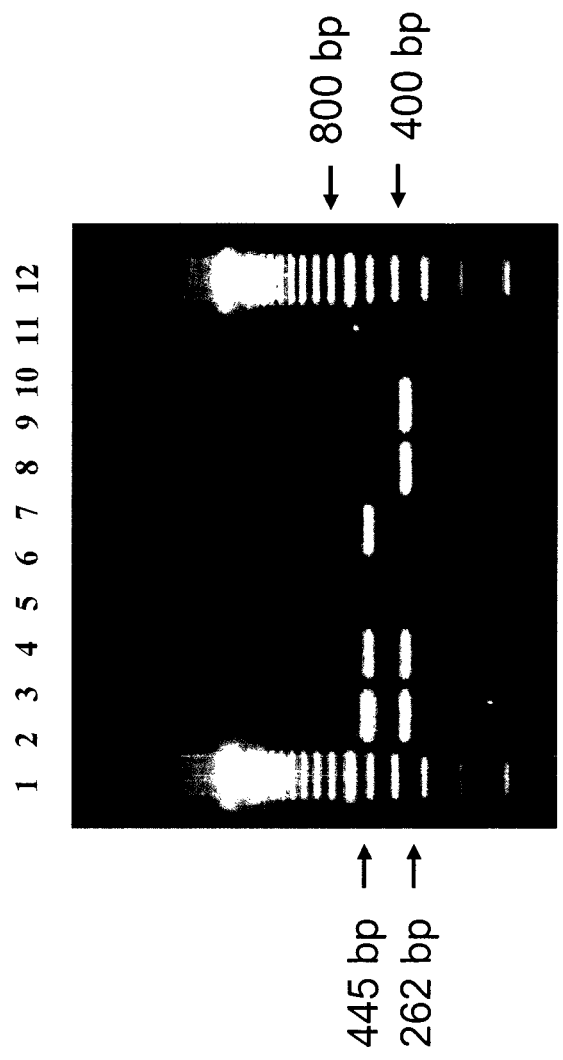
FIG. 2: Represents Results Obtained by the PCR Identification Protocol Developed for EE-GH5. Loading sequence of the gel: Lane 1: Molecular weight marker (100 bp ladder); lanes 2 to 3: DNA samples from cotton plants comprising the transgenic event EE-GH5; lanes 4 to 10: DNA samples from transgenic cotton plants not comprising elite event EE-GH5, but comprising a similar insect-resistance gene; lane 11: no template DNA control; lane 12: molecular weight marker.

FIG. 2 illustrates the result obtained with the elite event PCR identification protocol 1 for EE-GH5 on a number of cotton plant samples. The samples in lanes 2 to 3 were found to contain the elite event as the 305 bp band is detected, while the samples in lanes 4 to 10 do not comprise EE-GH5. Lanes 4 and 10 comprise other cotton elite events (including plants comprising different insect tolerance chimeric genes); lane 11 represents the negative control (water) sample, and lanes 1 and 12 represent the Molecular Weight Marker (100 bp ladder).

4. Use of a Specific Integration Fragment as a Probe for Detection of Material Comprising EE-GH5

A specific integration fragment of EE-GH5 is obtained by PCR amplification using specific primers GHI047 (SEQ ID No. 10) and GHI048 (SEQ ID No. 11) or by chemical synthesis and is labeled. This integration fragment is used as a specific probe for the detection of EE-GH5 in biological samples. Nucleic acid is extracted from the samples according to standard procedures. This nucleic acid is then contacted with the specific probe under hybridization conditions which are optimized to allow formation of a hybrid. The formation of the hybrid is then detected to indicate the presence of EE-GH5 nucleic acid in the sample. Optionally, the nucleic acid in the samples is amplified using the specific primers prior to contact with the specific probe. Alternatively, the nucleic acid is labeled prior to contact with the specific probe instead of the integration fragment. Optionally, the specific probe is attached to a solid carrier (such as, but not limited to a filter, strip or beads), prior to contact with the samples.

5. Protocol for the PCR-Based Determination of the Zygosity Status of EE-GH5 Cotton Plant Material 5.1. Primers Two primers recognizing the nucleotide sequences of the wild-type locus prior to insertion of the elite event, were designed in such a way that they are directed towards each other and have the insertion site in-between. This set of primers, together with a third primer complementary to foreign DNA sequences and directed towards the flanking DNA, allow simultaneous PCR amplification of the EE-GH5 locus as well as of the wt locus.

The following primers were found to give particularly clear and reproducible results in a zygosity scoring PCR reaction on EE-GH5 DNA:

```
                                      (SEQ ID No.: 9)
GHI066   5'-AgA.TAA.AAT.CgT.CAg.TgC.Tg-3'

(target: plant DNA upstream of 5' flanking sequence)

(SEQ ID No.: 3)
GHI057   5'-ATA.gCg.CgC.AAA.CTA.ggA-3'

(target: insert DNA)

(SEQ ID No.: 6)
GHI065   5'-ggg.CCg.gAT.AAA.ATT.AgC.CT-3'

(target: plant DNA of the 3' flanking sequence)
```

5.2. Amplified Fragments

The expected amplified fragments in the PCR reaction are:
For primer pair GHI065-GHI066: 517 bp (wild-type locus)
For primer pair GH1057-GHI065: 369 bp (EE-GH5 locus)

5.3. Template DNA

Template DNA was prepared from a leaf punch according to Edwards et al. (Nucleic Acid Research, 19, p 1349, 1991). When using DNA prepared with other methods, a test run utilizing different amounts of template should be done. Usually 50 ng of genomic template DNA yields the best results.

5.4. Assigned Positive and Negative Controls

To avoid false positives or negatives, it is advisable that the following positive and negative controls should be included in a PCR run:

Master Mix control (DNA negative control). This is a PCR in which no DNA is added to the reaction. When the expected result, no PCR products, is observed this indicates that the PCR cocktail was not contaminated with target DNA.

A DNA positive control (genomic DNA sample known to contain the transgenic sequences). Successful amplification of this positive control demonstrates that the PCR was run under conditions which allow for the amplification of target sequences.

A wild-type DNA control. This is a PCR in which the template DNA provided is genomic DNA prepared from a non-transgenic plant. When the expected result, no amplification of a transgene PCR product but amplification of the endogenous PCR product, is observed this indicates that there is no detectable transgene background amplification in a genomic DNA sample.

5.5. PCR Conditions

Optimal results were obtained under the following conditions:

the PCR mix for 25 µl reactions contains:
x µl template DNA (150 ng)
2.5 µl 10× Amplification Buffer (supplied by the manufacturer with the Taq polymerase)
0.5 µl 10 mM dNTP's
1.5 µl GHI053 (10 pmoles/µl)
1.0 µl GHI054 (10 pmoles/µl)
0.5 µl GHI041 (10 pmoles/µl)
0.1 µl Taq DNA polymerase (5 units/µl)
water up to 25 µl the thermocycling profile to be followed for optimal results is the following:
4 min. at 95° C.
Followed by:
1 min. at 95° C.
1 min. at 57° C.
2 min. at 72° C.
For 5 cycles
Followed by:
30 sec. at 92° C.
30 sec. at 57° C.
1 min. at 72° C.
For 25 cycles
Followed by:
10 minutes at 72° C.

5.6. Agarose Gel Analysis

To optimally visualise the results of the PCR it was determined that between 10 and 20 µl of the PCR samples should be applied on a 1.5% agarose gel (Tris-borate buffer) with an appropriate molecular weight marker (e.g. 100 bp ladder PHARMACIA).

5.7. Validation of the Results

Data from transgenic plant DNA samples within a single PCR run and a single PCR Master Mix will not be acceptable unless:

the positive control shows the expected PCR products (transgenic target amplification)

the wild-type-positive DNA control shows the expected result (wild-type target amplification).

the negative control is negative for PCR amplification (no fragments).

Lanes showing visible amounts of the transgenic PCR product of the expected size and not showing visible amounts of the wild type PCR product, indicate that the corresponding plant from which the genomic DNA template was prepared, is homozygous for the transgenic gene cassette.

Lanes showing visible amounts of the transgenic and wild type PCR products of the expected sizes, indicate that the corresponding plant from which the genomic template DNA was prepared, is hemizygous for the transgenic gene cassette.

Lanes not showing visible amounts of the transgenic PCR product and showing visible amounts of the wild type PCR product, indicate that the corresponding plant from which the genomic template DNA was prepared, has not inherited the transgenic sequence assayed for and is thus homozygous for the wild type locus.

Lanes not showing visible amounts of transgenic and wild type PCR products, indicate that the quality and/or quantity of the genomic DNA didn't allow for a PCR product to be generated. These plants cannot be scored. The genomic DNA preparation should be repeated and a new PCR run, with the appropriate controls, has to be performed.

5.8. Use of the Zygosity Scoring Protocol for Identification of Zygosity Status in EE-GH5 Containing Plants.

Figure 3:
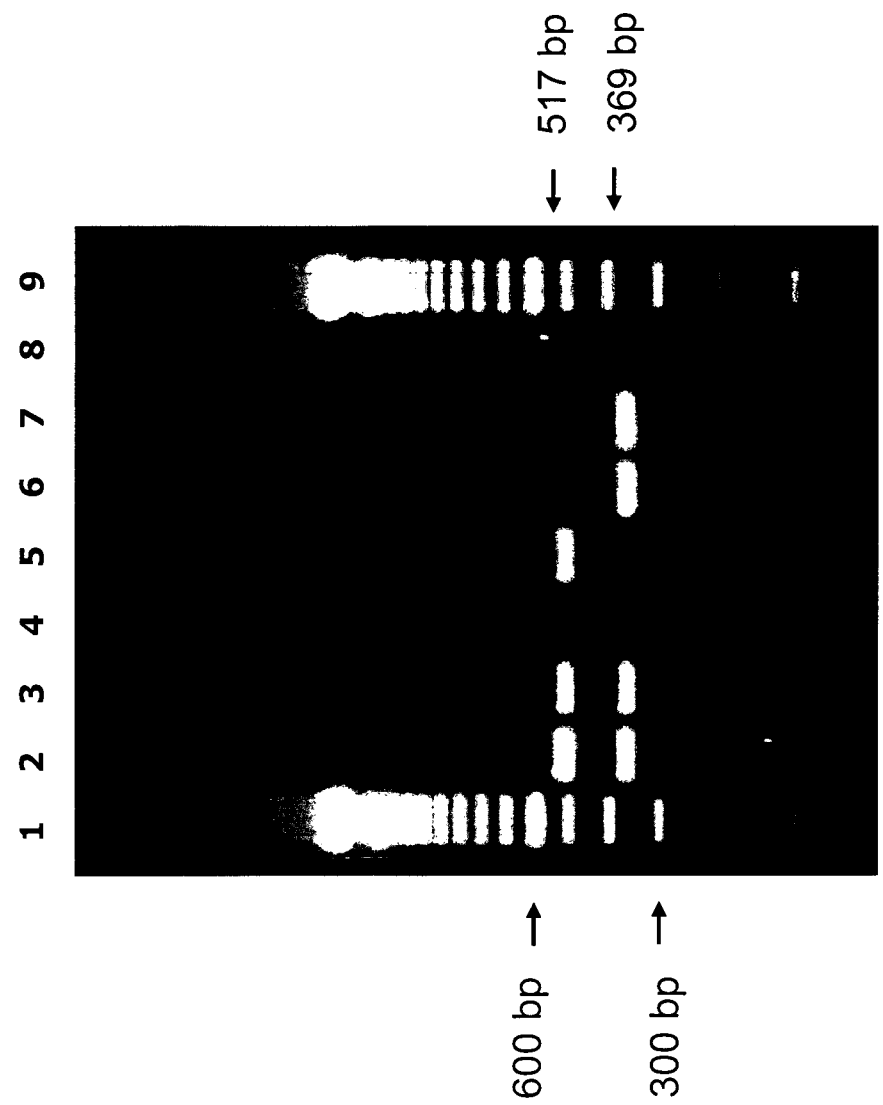
FIG. 3: Represents Results Obtained by the Zygosity Scoring PCR Protocol Developed for EE-GH5. Loading sequence of the gel: Lane 1: Molecular weight marker (100 bp ladder); lanes 2 and 3: DNA samples from cotton plants comprising the transgenic event EE-GH5 in heterozygous form; lanes 4: Fail Lane 5: control DNA sample from wild-type cotton plant; lanes 6-7: DNA sample from cotton plants comprising the transgenic event EE-GH5 in homozygous form lane 8: no template DNA control; lane 9: molecular weight marker.

FIG. 3 illustrates the result obtained with the zygosity scoring PCR for EE-GH5 on a number of cotton plant samples. The samples in lanes 2-3 and 6-7 were found to contain the PCR fragment (369 bp) characteristic for elite event EE-GH5, while the samples in lanes 2, 3 and 5 contained the fragment characteristic for the presence of the wt locus. Lanes 6 and 7 therefore contain EE-GH5 in homozygous form, lanes 2 and 3 contain EE-GH5 in hemizygous form and lane 5 contains the wt locus in homozygous form (azygous for EE-GH5). Lane 8 represents the negative control (water) sample, and lanes 1 and 9 represent the Molecular Weight Marker (100 bp ladder).

6. Introgression of EE-GH5 into Preferred Cultivars

Elite event EE-GH5 is introduced by repeated back-crossing into commercial cotton cultivars such as but not limited to FM5013, FM5015, FM5017, FM989, FM832, FM966 and FM958, FM989, FM958, FM832, FM991, FM819, FM800, FM960, FM966, FM981, FM5035, FM5044, FM5045, FM5013, FM5015, FM5017 or FM5024.

It is observed that the introgression of the elite event into these cultivars does not significantly influence any of the desirable phenotypic or agronomic characteristics of these cultivars (no linkage drag) while expression of the transgene, as determined by glufosinate tolerance, meets commercially acceptable levels. This confirms the status of event EE-GH5 as an elite event.

Elite event may be advantageously combined with other elite events available in the market, particularly other elite event insect resistance gene for the purpose of insect resistance management, such as but not limited to event 3006-210-23; (USDA aphis petition 03-036-02p) event 281-24-236 (USDA aphis petition 03-036-01p); event MON158985 (USDA aphis petition 00-342-01p); event MON531 (USDA aphis petition 94-308-01p) or event COT102 (=Syngenta vip3A) USDA aphis petition 03-155-01p. Elite event EE_GH5 can also be combined with herbice tolerant elite events such as event MON1445 (USDA aphis petition 95-045-01p) or event MON88913 (USDA aphis petition 04-086-01p).

As used in the claims below, unless otherwise clearly indicated, the term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts.

Reference seed comprising elite event EE-GH5 was deposited as EE-GH5 at the ATCC (10801 University Blvd., Manassas, Va. 20110-2209) on Jan. 22, 2007, under ATCC accession number PTA-8171. An alternative name for EE-GH5 is T304-40

As used in the claims below, unless otherwise clearly indicated, the term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts.

The above description of the invention is intended to be illustrative and not limiting.

Various changes or modifications in the embodiments described may occur to those skilled in the art. These can be made without departing from the spirit or scope of the invention.

The invention claimed is:

1. A method for identifying elite event EE-GH5 in biological samples, comprising amplifying a nucleic acid present in said biological samples with at least two primers, wherein one of said primers recognizes the 5' or 3' flanking region of EE-GH5 and the other primer recognizes the foreign DNA of EE-GH5 contiguous therewith, said 5' flanking region comprises the nucleotide sequence of SEQ ID No. 1 from nucleotide 1 to nucleotide 98 or the nucleotide sequence of SEQ ID No. 16 from nucleotide 1 to nucleotide 563 and said foreign DNA contiguous with said 5' flanking region comprises the complement of SEQ ID No. 1 from nucleotide 99 to nucleotide 334, said 3' flanking region comprises the nucleotide sequence of the complement of SEQ ID No. 2 from nucleotide 41 to nucleotide 452 and said foreign DNA contiguous with said 3' flanking region comprises the nucleotide sequence of SEQ ID No. 2 from nucleotide 1 to nucleotide 40.

2. The method of claim 1, wherein said method comprises amplifying a DNA fragment of between 100 and 500 bp from a nucleic acid present in said biological samples using a polymerase chain reaction with said at least two primers.

3. The method of claim 2, wherein said primer recognizing the 5' flanking region consist of a nucleotide sequence of 17 to 200 consecutive nucleotides selected from the nucleotide sequence of SEQ ID No. 1 from nucleotide 1 to nucleotide 98 or the nucleotide sequence of SEQ ID No. 16 from nucleotide 1 to nucleotide 563 or said primer recognizing the 3' flanking region of EE-GH5 consist of a nucleotide sequence of 17 to 200 consecutive nucleotides selected from the nucleotide sequence of the complement of SEQ ID No. 2 from nucleotide 41 to nucleotide 452, and said primer recognizing a sequence within the foreign DNA consists of 17 to 200 consecutive nucleotides selected from the nucleotide sequence of the complement of SEQ ID No. 1 from nucleotide 99 to nucleotide 334 or the nucleotide sequence of SEQ ID No. 2 from nucleotide 1 to nucleotide 40.

4. The method of claim 2, wherein said primer recognizing the 5' flanking region comprises at its extreme 3' end a nucleotide sequence of at least 17 consecutive nucleotides selected from the nucleotide sequence of SEQ ID No. 1 from nucleotide 1 to nucleotide 98 or the nucleotide sequence of SEQ ID No. 16 from nucleotide 1 to nucleotide 563 or said primer recognizing the 3' flanking region of EE-GH5 comprises at its extreme 3' end a nucleotide sequence of at least 17 consecutive nucleotides selected from the nucleotide sequence of the complement of SEQ ID No. 2 from nucleotide 41 to nucleotide 452, and said primer recognizing a sequence within the foreign DNA comprises at its 3' end at least 17 consecutive nucleotides selected from the nucleotide sequence of the complement of SEQ ID No. 1 from nucleotide 99 to nucleotide 334 or the nucleotide sequence of SEQ ID No. 2 from nucleotide 1 to nucleotide 40.

5. The method of claim 2, wherein said primers comprise the sequence of SEQ ID No. 3 and SEQ ID No. 6, respectively.

6. The method of claim 2, wherein said method comprises amplifying a fragment of about 369 bp.

7. A kit for identifying elite event EE-GH5 in biological samples, said kit comprising one primer recognizing the 5' flanking region of EE-GH5, said 5' flanking region having the nucleotide sequence of SEQ ID No. 1 from nucleotide 1 to nucleotide 98 or the nucleotide sequence of SEQ ID No. 16 from nucleotide 1 to nucleotide 563 or one primer recognizing the 3' flanking region of EE-GH5, said 3' flanking region having the nucleotide sequence of the complement of SEQ ID No. 2 from nucleotide 41 to nucleotide 452 and one primer recognizing a sequence within the foreign DNA, said foreign DNA having the nucleotide sequence of the complement of SEQ ID No. 1 from nucleotide 99 to nucleotide 334 or the nucleotide sequence of SEQ ID No. 2 from nucleotide 1 to nucleotide 40, wherein the 5' end of at least one of said primers comprises one or more mismatches or a nucleotide sequence unrelated to said flanking sequence or said foreign DNA.

8. The kit of claim 7, wherein said primer recognizing the 5' flanking region consists at its 3' end of a nucleotide sequence of 17 to 200 consecutive nucleotides comprising the nucleotide sequence of SEQ ID No. 1 from nucleotide 1 to nucleotide 98 or the nucleotide sequence of SEQ ID No. 16 from nucleotide 1 to nucleotide 563 or said primer recognizing the 3' flanking region of EE-GH5 consists at its 3' end of a nucleotide sequence of 17 to 200 consecutive nucleotides of the complement of SEQ ID No. 2 from nucleotide 41 to nucleotide 452, and said primer recognizing a sequence within the foreign DNA consists at its 3' end of 17 to 200 consecutive nucleotides comprising the nucleotide sequence of the complement of SEQ ID No. 1 from nucleotide 99 to nucleotide 334 or the nucleotide sequence of SEQ ID No. 2 from nucleotide 1 to nucleotide 40.

9. The kit of claim 7, wherein said primer recognizing the 5' flanking region comprises at its extreme 3' end a nucleotide sequence of at least 17 consecutive nucleotides selected from the nucleotide sequence of SEQ ID No. 1 from nucleotide 1 to nucleotide 98 or the nucleotide sequence of SEQ ID No. 16 from nucleotide 1 to nucleotide 563 or said primer recognizing the 3' flanking region of EE-GH5 comprises at its extreme 3' end a nucleotide sequence of at least 17 consecutive nucleotides selected from the nucleotide sequence of the complement of SEQ ID No. 2 from nucleotide 41 to nucleotide 452, and said primer recognizing a sequence within the foreign DNA comprises at its 3' end at least 17 consecutive nucleotides selected from the nucleotide sequence of the complement of SEQ ID No. 1 from nucleotide 99 to nucleotide 334 or the nucleotide sequence of SEQ ID No. 2 from nucleotide 1 to nucleotide 40.

10. The kit of claim 7, comprising a primer consisting at its 3' end of the sequence of SEQ ID No. 3, and a primer consisting at its 3' end of the sequence of SEQ ID No. 6.

11. A method for identifying elite event EE-GH5 in biological samples comprising hybridizing a nucleic acid of biological samples with a specific probe that recognizes a part of the 5' or 3' flanking region of EE-GH5 and a part of the foreign DNA of EE-GH5 contiguous therewith, said 5' flanking region comprises the nucleotide sequence of SEQ ID No. 1 from nucleotide 1 to nucleotide 98 or the nucleotide sequence of SEQ ID No. 16 from nucleotide 1 to nucleotide 563 and said foreign DNA contiguous with said 5' flanking region comprises the complement of SEQ ID No. 1 from nucleotide 99 to nucleotide 334, said 3' flanking region comprises the nucleotide sequence of the complement of SEQ ID No. 2 from nucleotide 41 to nucleotide 452 and said foreign DNA contiguous with said 3' flanking region comprises the nucleotide sequence of SEQ ID No. 2 from nucleotide 1 to nucleotide 40.

12. The method of claim 11, wherein the sequence of said specific probe has at least 80% sequence identity with a sequence comprising part of the 5' flanking sequence or the 3' flanking sequence of EE-GH5 and the sequence of the foreign DNA contiguous therewith.

13. The method of claim 12, wherein the sequence of said specific probe has at least 80% sequence identity with SEQ ID No. 1 from nucleotide 78 to 119 or SEQ ID No. 2 from nucleotide 20 to 61, or the complement of said sequences.

14. A kit for identifying elite event EE-GH5 in biological samples, said kit comprising a specific probe, capable of hybridizing specifically to part of the 5' or 3' flanking region of EE-GH5 and a part of the foreign DNA of EE-GH5 contiguous therewith, said 5' flanking region comprises the nucleotide sequence of SEQ ID No. 1 from nucleotide 1 to nucleotide 98 or the nucleotide sequence of SEQ ID No. 16 from nucleotide 1 to nucleotide 563 and said foreign DNA contiguous with said 5' flanking region comprises the complement of SEQ ID No. 1 from nucleotide 99 to nucleotide 334, said 3' flanking region comprises the nucleotide sequence of the complement of SEQ ID No. 2 from nucleotide 41 to nucleotide 452 and said foreign DNA contiguous with said 3' flanking region comprises the nucleotide sequence of SEQ ID No. 2 from nucleotide 1 to nucleotide 40, wherein said probe comprises part of the 5' flanking sequence and part of the sequence of the foreign DNA contiguous therewith, or the complement thereof, or part of the 3' flanking sequence of EE-GH5 and part of the sequence of the foreign DNA contiguous therewith, or the complement thereof.

15. The kit of claim 14, wherein the sequence of said specific probe has at least 80% sequence identity with a sequence comprising part of the 5' flanking sequence or the 3' flanking sequence of EE-GH5 and the sequence of the foreign DNA contiguous therewith.

16. The kit of claim 15, wherein the sequence of said specific probe has at least 80% sequence identity with SEQ ID No. 1 from nucleotide 78 to 119 or SEQ ID No. 2 from nucleotide 20 to 61, or the complement of said sequences.

17. A specific probe for the identification of elite event EE-GH5 in biological samples, wherein said elite event has a specific region comprising a 5' flanking region and inserted foreign DNA contiguous therewith and a specific region comprising a 3' flanking region and inserted foreign DNA contiguous therewith, said 5' flanking region comprises the nucleotide sequence of SEQ ID No. 1 from nucleotide 1 to nucleotide 98 or the nucleotide sequence of SEQ ID No. 16 from nucleotide 1 to nucleotide 563 and said foreign DNA contiguous with said 5' flanking region comprises the complement of SEQ ID No. 1 from nucleotide 99 to nucleotide 334, said 3' flanking region comprises the nucleotide sequence of the complement of SEQ ID No. 2 from nucleotide 41 to nucleotide 452 and said foreign DNA contiguous with said 3' flanking region comprises the nucleotide sequence of SEQ ID No. 2 from nucleotide 1 to nucleotide 40, wherein said probe comprises part of the 5' flanking sequence and part of the sequence of the foreign DNA contiguous therewith, or the complement thereof, or part of the 3' flanking sequence of EE-GH5 and part of the sequence of the foreign DNA contiguous therewith, or the complement thereof.

18. The probe of claim 17, which has at least 80% sequence identity with a sequence comprising part of the 5' flanking sequence or the 3' flanking sequence of EE-GH5 and the sequence of the foreign DNA contiguous therewith, or the complement thereof.

19. The probe of claim 18, which has at least 80% sequence identity with SEQ ID No. 1 from nucleotide 78 to 119 or SEQ ID No. 2 from nucleotide 20 to 61, or the complement of said sequences.

20. A method for confirming seed purity comprising
(a) (i) amplifying a nucleic sequence present in a seed sample using at least two primers, wherein one of said primers recognizes the 5' or 3' flanking region of EE-GH5 and the other primer recognizes the foreign DNA of EE-GH5 contiguous therewith, or (ii) hybridizing a nucleic sequence present in a seed sample with a specific probe that recognizes a part of the 5' or 3' flanking sequence of EE-GH5 and a part of the foreign DNA of EE-GH5 contiguous therewith,
said 5' flanking region comprises the nucleotide sequence of SEQ ID No. 1 from nucleotide 1 to nucleotide 98 or the nucleotide sequence of SEQ ID No. 16 from nucleotide 1 to nucleotide 563 and said foreign DNA contiguous with said 5' flanking region comprises the complement of SEQ ID No. 1 from nucleotide 99 to nucleotide 334, said 3' flanking region comprises the nucleotide sequence of the complement of SEQ ID No. 2 from nucleotide 41 to nucleotide 452 and said foreign DNA contiguous with said 3' flanking region comprises the nucleotide sequence of SEQ ID No. 2 from nucleotide 1 to nucleotide 40; and
(b) confirming purity of said seed sample.

21. A method for screening seeds for the presence of EE-GH5
(a) (i) amplifying a nucleic sequence present in a seed sample using at least two primers, wherein one of said primers recognizes the 5' or 3' flanking region of EE-GH5 and the other primer recognizes the foreign DNA of EE-GH5 contiguous therewith, or (ii) hybridizing a nucleic sequence present in a seed sample with a specific probe that recognizes a part of the 5' or 3' flanking sequence of EE-GH5 and a part of the foreign DNA of EE-GH5 contiguous therewith,
said 5' flanking region comprises the nucleotide sequence of SEQ ID No. 1 from nucleotide 1 to nucleotide 98 or the nucleotide sequence of SEQ ID No. 16 from nucleotide 1 to nucleotide 563 and said foreign DNA contiguous with said 5' flanking region comprises the complement of SEQ ID No. 1 from nucleotide 99 to nucleotide 334, said 3' flanking region comprises the nucleotide sequence of the complement of SEQ ID No. 2 from nucleotide 41 to nucleotide 452 and said foreign DNA contiguous with said 3' flanking region comprises the nucleotide sequence of SEQ ID No. 2 from nucleotide 1 to nucleotide 40; and
(b) screening said seed sample for the presence of elite event EE-GH5.

22. A method of detecting the presence of elite event EE-GH5 in biological samples through hybridization with a substantially complementary labeled nucleic acid probe in which the probe:target nucleic acid ratio is amplified through recycling of the target nucleic acid sequence, said method comprising:
a) hybridizing said target nucleic acid sequence to a first nucleic acid oligonucleotide comprising the nucleotide sequence of SEQ ID No. 1 from nucleotide 99 to nucleotide 116 or its complement or said first nucleic acid oligonucleotide comprising the nucleotide sequence of SEQ ID No. 2 from nucleotide 23 to nucleotide 40 or its complement;
b) hybridizing said target nucleic acid sequence to a second nucleic acid oligonucleotide comprising the nucleotide sequence of SEQ ID No. 1 from nucleotide 81 to nucleotide 98 or its complement or said labeled nucleic acid probe comprising the nucleotide sequence of SEQ ID No. 2 from nucleotide 41 to nucleotide 58 or its complement, wherein said first and second oligonucleotide overlap by at least one nucleotide and wherein either said first or said second oligonucleotide is labeled to be said labeled nucleic acid probe;
c) cleaving only the labeled probe within the probe:target nucleic acid sequence duplex with an enzyme which causes selective probe cleavage resulting in duplex disassociation, leaving the target sequence intact;
d) recycling of the target nucleic acid sequence by repeating steps (a) to (c); and e) detecting cleaved labeled probe, thereby determining the presence of said target nucleic acid sequence.

23. An isolated nucleic acid molecule comprising (i) a nucleotide sequence having at least 75% sequence identity to SEQ ID No. 1 from nucleotide 88 to nucleotide 109 or SEQ ID No. 2 from nucleotide 30 to nucleotide 50, or the complement of said sequences; or (ii) the nucleotide sequence of SEQ ID No. 12.

24. The isolated nucleic acid molecule of claim 23 comprising a nucleotide sequence having at least 75% sequence identity to SEQ ID No. 1 from nucleotide 78 to nucleotide 119 or SEQ ID No. 2 from nucleotide 20 to nucleotide 60, or the complement of said sequences.

25. The method of claim 1, comprising amplifying a DNA fragment of about 262 bp using primers consisting essentially of the nucleotides sequences of SEQ ID No. 10 and SEQ ID No. 11 respectively.

26. The kit of claim 7, comprising two oligonucleotide primers consisting essentially of, at their 3' end, the nucleotides sequences of SEQ ID No. 10 and SEQ ID No. 11 respectively.

27. An isolated nucleic acid molecule comprising (i) a nucleotide sequence at least 90% sequence identity to SEQ ID No. 1 from nucleotide 88 to nucleotide 109 or SEQ ID No. 2 from nucleotide 30 to nucleotide 50, or the complement of said sequences; or (ii) the nucleotide sequence of SEQ ID No. 12.

28. The isolated nucleic acid molecule of claim 23 comprising a nucleotide sequence having at least 90% sequence identity to SEQ ID No. 1 from nucleotide 78 to nucleotide 119 or SEQ ID No. 2 from nucleotide 20 to nucleotide 60, or the complement of said sequences.

29. The method of claim 7, wherein the 5' end of at least one of said primers comprises one or more mismatches.

30. The method of claim 7, wherein the 5' end of at least one of said primers comprises a nucleotide sequence unrelated to said flanking sequence or said foreign DNA.

31. A kit for identifying elite event EE-GH5 in biological samples, said kit comprising one primer recognizing the 5' flanking region of EE-GH5, said 5' flanking region having the nucleotide sequence of SEQ ID No. 1 from nucleotide 1 to nucleotide 98 or the nucleotide sequence of SEQ ID No. 16 from nucleotide 1 to nucleotide 563 or one primer recognizing the 3' flanking region of EE-GH5, said 3' flanking region having the nucleotide sequence of the complement of SEQ ID No. 2 from nucleotide 41 to nucleotide 452 and one primer recognizing a sequence within the foreign DNA, said foreign DNA having the nucleotide sequence of the complement of SEQ ID No. 1 from nucleotide 99 to nucleotide 334 or the nucleotide sequence of SEQ ID No. 2 from nucleotide 1 to nucleotide 40, wherein at least one of said primers is modified with a label.

* * * * *

SEQUENCE LISTING

<160> NUMBER OF SEQ ID NOS: 19

<210> SEQ ID NO 1
<211> LENGTH: 334
<212> TYPE: DNA
<213> ORGANISM: Artificial Sequence
<220> FEATURE:
<223> OTHER INFORMATION: Nucleotide sequence comprising the 5' flanking
      sequence of EE-GH5
<220> FEATURE:
<221> NAME/KEY: misc_feature
<222> LOCATION: (1)..(98)
<223> OTHER INFORMATION: plant DNA
<220> FEATURE:
<221> NAME/KEY: misc_feature
<222> LOCATION: (99)..(334)
<223> OTHER INFORMATION: insert DNA

<400> SEQUENCE: 1
cttttatcat ataagtgcct atataaataa agtttagtca gtcaaattag agagattgtc      60
attgtaggga gtttgtccaa ttattggtgt ttttaatccc agtactcggc cgtcgaccgc     120
ggtaccccgg aattgaaaac agatttgagg tttcaaagtg gtgttgtggc tacagttcaa     180
gaggcattaa aagctgattt ggccggatct tttgaagctt tcaaacacaa ggaaatcatc     240
catcaacctc caatcgaatg gcttttttgct tggcacaata attcccctac tttcgacttg    300
aggacaagtc gattttccgg gccggatgta ttga                                 334

<210> SEQ ID NO 2
<211> LENGTH: 452
<212> TYPE: DNA
<213> ORGANISM: Artificial Sequence
<220> FEATURE:
<223> OTHER INFORMATION: Nucleotide sequence comprising the 3' flanking
      sequence of EE-GH5
<220> FEATURE:
<221> NAME/KEY: misc_feature
<222> LOCATION: (1)..(40)
<223> OTHER INFORMATION: insert DNA
<220> FEATURE:
<221> NAME/KEY: misc_feature
<222> LOCATION: (41)..(452)
<223> OTHER INFORMATION: plant DNA

<400> SEQUENCE: 2
atagcgcgca aactaggata aattatcgcg cgcggtgtca tctatctcct ttttcttttc      60
aagttatccc aagatctagg ggtattttgc atcattaaga gaaaactttg tttaattaga     120
cttccaatca ccagtcttag gtataaggga aggctgatgc cgataacatt gccgaacaaa     180
ccatcaaggc aactagagat gccttgatgc aaaagagctc ttttttagac cctcaaatgc     240
caagcagtgg atagaaagaa gctcaatgtt aagtgcaaac aaaattcgaa aggctaaaag     300
tttatcgaga ttcgaatctc taaatcaatg tcattaacaa ctatataaca ggctaatttt     360
atccggccca ataataaaa caaaataaaa ataataaatc aaggtcaatt tacaaaatag      420
attggcccaa acaaaaaaga gcccaataac cc                                   452

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide primer GHI057

<400> SEQUENCE: 3
atagcgcgca aactagga                                                    18

```
<210> SEQ ID NO 4
<211> LENGTH: 20
<212> TYPE: DNA
<213> ORGANISM: Artificial Sequence
<220> FEATURE:
<223> OTHER INFORMATION: Oligonucleotide primer MAE115

<400> SEQUENCE: 4
tcggcaatgt tatcggcatc                                              20

<210> SEQ ID NO 5
<211> LENGTH: 19
<212> TYPE: DNA
<213> ORGANISM: Artificial Sequence
<220> FEATURE:
<223> OTHER INFORMATION: Oligonucleotide primer HVH022

<400> SEQUENCE: 5
ccactgcttg gcatttgag                                               19

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide primer GHI065

<400> SEQUENCE: 6
gggccggata aaattagcct                                              20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide primer HVH024

<400> SEQUENCE: 7
gtcattgtag ggagtttgtc                                              20

<210> SEQ ID NO 8
<211> LENGTH: 18
<212> TYPE: DNA
<213> ORGANISM: Artificial Sequence
<220> FEATURE:
<223> OTHER INFORMATION: Oligonucleotide primer DPA312

<400> SEQUENCE: 8
tgcctcttga actgtagc                                                18

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide primer GHI066

<400> SEQUENCE: 9
agataaaatc gtcagtgctg                                              20

<210> SEQ ID NO 10
<211> LENGTH: 18
<212> TYPE: DNA
<213> ORGANISM: Artificial Sequence
<220> FEATURE:
```

<223> OTHER INFORMATION: Oligonucleotide primer GHI047

<400> SEQUENCE: 10
tgcctcttga actgtagc                                                        18

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer GHI048

<400> SEQUENCE: 11
acttgcagtt gctgatgatg                                                      20

<210> SEQ ID NO 12
<211> LENGTH: 262
<212> TYPE: DNA
<213> ORGANISM: Artificial Sequence
<220> FEATURE:
<223> OTHER INFORMATION: Nucleotide sequence of the fragment amplified
      from cotton DNA comprising EE-GH5 using GHI047 and GHI048
<220> FEATURE:
<221> NAME/KEY: misc_feature
<222> LOCATION: (1)..(51)
<223> OTHER INFORMATION: sequence derived from 3' me1
<220> FEATURE:
<221> NAME/KEY: misc_feature
<222> LOCATION: (86)..(88)
<223> OTHER INFORMATION: sequence derived from right T-DNA border
<220> FEATURE:
<221> NAME/KEY: misc_feature
<222> LOCATION: (89)..(262)
<223> OTHER INFORMATION: sequence derived from 3' me1

<400> SEQUENCE: 12
tgcctcttga actgtagcca caacaccact ttgaaacctc aaatctgttt tcaattccgg          60
ggtaccgcgg tcgacggccg agtactggcc aaatttagtt tttggataaa gtaccagatt        120
tagggcaata aaactataaa cggccagctt ttagctacat acaatgagca ttcctgataa        180
acaaagaacc caaccggtat ttgtaagtga ataaacaaaa gtagtattaa gctttaagtt        240
tccatcatca gcaactgcaa gt                                                 262

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide primer GHI001

<400> SEQUENCE: 13
aacctaggct gctgaaggag c                                                    21

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide primer GHI002

<400> SEQUENCE: 14
caactcctcc agtcatctcc g                                                    21

<210> SEQ ID NO 15
<211> LENGTH: 558
<212> TYPE: DNA

```
<213> ORGANISM: Artificial Sequence
<220> FEATURE:
<223> OTHER INFORMATION: Nucleotide sequence of the plant genomic target
      sequence prior to insertion of EE-GH5
<220> FEATURE:
<221> NAME/KEY: misc_feature
<222> LOCATION: (1)..(113)
<223> OTHER INFORMATION: sequence corresponding to the 5' flanking
      sequence
<220> FEATURE:
<221> NAME/KEY: misc_feature
<222> LOCATION: (114)..(145)
<223> OTHER INFORMATION: pre-insertion deletion in elite event EE-GH5
<220> FEATURE:
<221> NAME/KEY: misc_feature
<222> LOCATION: (146)..(558)
<223> OTHER INFORMATION: sequence corresponding to the 3' flanking
      sequence
<220> FEATURE:
<221> NAME/KEY: misc_feature
<222> LOCATION: (457)..(475)
<223> OTHER INFORMATION: sequence corresponding to the complement of
      oligonucleotide GHI065

<400> SEQUENCE: 15
agtttatatt tcttactttt atcatataag tgcctatata aataaagttt agtcagtcaa      60
attagagaga ttgtcattgt agggagtttg tccaattatt ggtgttttta atcacaagtt     120
gtttaaggat tccaaaccat acattatcta tctcctttttt cttttcaagt tatcccaaga    180 tctagggta ttttgcatca ttaagagaaa actttgttta attagacttc caatcaccag      240
tcttaggtat aagggaaggc tgatgccgat aacattgccg aacaaaccat caaggcaact    300
agagatgcct tgatgcaaaa gagctcttttt ttagaccctc aaatgccaag cagtggatag   360
aaagaagctc aatgttaagt gcaaacaaaa ttcgaaaggc taaaagttta tcgagattcg    420
aatctctaaa tcaatgtcat taacaactat ataacaggct aatttatcc ggcccaataa     480 ataaaacaaa ataaaaataa taaatcaagg tcaatttaca aaatagattg gcccaaacaa    540
aaaagagccc aataaccc                                                   558

<210> SEQ ID NO 16
<211> LENGTH: 799
<212> TYPE: DNA
<213> ORGANISM: Artificial Sequence
<220> FEATURE:
<223> OTHER INFORMATION: Nucleotide sequence comprising the 5' flanking
      sequence of EE-GH5 (long)
<220> FEATURE:
<221> NAME/KEY: misc_feature
<222> LOCATION: (1)..(563)
<223> OTHER INFORMATION: plant DNA
<220> FEATURE:
<221> NAME/KEY: misc_feature
<222> LOCATION: (564)..(799)
<223> OTHER INFORMATION: insert DNA

<400> SEQUENCE: 16
aacaaataag ccaattccaa agagaggata gctgatcttt tcactaatca taacttgaat     60 tttttagtg gtgcttatct gtttcaggtg ttaggagcac aatcatacca ttccctgcat     120
aattttcaga ctctaggatg aatccttttc gaagaggagg tgaatgatac gaactcagaa    180
agggtaaatt catttgagtt caagtttgga acactgacca acttgcaatg aattttttggg   240 ttaaattatt ttctttatgg atcatgaaat gatatattat ttaaaatttt aagatgttta   300
tttattcatt taattatagt ttgattatat acatttgtaa aattgaatat ttatttggtt   360
ttaaaagtta ttaatttctt gtttattcat taaataaagt tcaattatag ataaaatcgt   420
```

```
cagtgctgaa ttttatatta ttttattaga agtttatatt tcttactttt atcatataag    480
tgcctatata aataaagttt agtcagtcaa attagagaga ttgtcattgt agggagtttg    540
tccaattatt ggtgttttta atcccagtac tcggccgtcg accgcggtac cccggaattg    600
aaaacagatt tgaggtttca aagtggtgtt gtggctacag ttcaagaggc attaaaagct    660
gatttggccg gatcttttga agctttcaaa cacaaggaaa tcatccatca acctccaatc    720
gaatggcttt ttgcttggca caataattcc cctactttcg acttgaggac aagtcgattt    780
tccgggccgg atgtattga                                                  799

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide primer HVH036

<400> SEQUENCE: 17
caggtgttag gagcacaatc                                                 20

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide primer SHA028

<400> SEQUENCE: 18
cacaacacca ctttgaaacc tcaa                                            24

<210> SEQ ID NO 19
<211> LENGTH: 19
<212> TYPE: DNA
<213> ORGANISM: Artificial Sequence
<220> FEATURE:
<223> OTHER INFORMATION: Oligonucleotide primer MAE067

<400> SEQUENCE: 19
ccattcgatt ggaggttga                                                  19
```